United States Patent
Huntoon et al.

[11] Patent Number: 5,906,879
[45] Date of Patent: May 25, 1999

[54] ULTRA RESILIENT THREE-DIMENSIONAL NONWOVEN FIBER MATERIAL AND PROCESS FOR PRODUCING THE SAME

[75] Inventors: Andrew Edsel Huntoon, Appleton, Wis.; Mary Garvie Weber, Alpharetta, Ga.; Gordon Allen Shaw, Greenville, Wis.; Marshall Kenneth Bryant, Lithonia, Ga.; Mark George Everson, Neenah, Wis.; Gerald Lewis Clark, Tucker; Wanda Walton Jackson, Alpharetta, both of Ga.; Susan Marie Vanage, Centerville, Ohio; Mark Charles Jacobs, Appleton, Wis.; Pamela Jean Mayberry; James Arthur Davis, both of Roswell, Ga.; Douglas Bryan Cole, Appleton, Wis.; Stanley Michael Gryskiewicz, Woodstock, Ga.; Ann Louise McCormack, Cumming, Ga.; Richard Daniel Pike, Norcross, Ga.; Leslie Warren Collier, IV, Roswell, Ga.; Frank Andrew Rosch, III, Sherwood, Wis.; Scott Richard Lange, Little Rock, Ark.

[73] Assignee: Kimberly-Clark Worldwide, Inc., Neenah, Wis.

[21] Appl. No.: 08/847,649

[22] Filed: Apr. 30, 1997

[51] Int. Cl.⁶ .................................................. B32B 3/10
[52] U.S. Cl. .................... 428/136; 264/103; 264/172.15; 264/210.2; 264/286; 428/152; 428/168; 428/171; 428/182; 442/361; 442/364
[58] Field of Search .................................. 428/136, 152, 428/155, 171, 168, 182, 184, 373, 167; 442/361, 364; 264/103, 172.15, 210.2, 286

[56] References Cited

U.S. PATENT DOCUMENTS

| | | |
|---|---|---|
| 3,085,575 | 4/1963 | DeWoskin . |
| 3,882,216 | 5/1975 | Delanty et al. . |
| 4,340,058 | 7/1982 | Pierce et al. . |
| 4,578,070 | 3/1986 | Holtman . |
| 5,151,091 | 9/1992 | Glaug et al. . |
| 5,167,654 | 12/1992 | Yang . |
| 5,180,620 | 1/1993 | Mende . |
| 5,197,959 | 3/1993 | Buell . |
| 5,382,245 | 1/1995 | Thompson et al. . |
| 5,476,459 | 12/1995 | Yang . |
| 5,505,720 | 4/1996 | Walters et al. . |
| 5,514,120 | 5/1996 | Johnston et al. . |
| 5,527,300 | 6/1996 | Sauer . |
| 5,536,555 | 7/1996 | Zelazoski et al. . |
| 5,576,090 | 11/1996 | Suzuki . |
| 5,702,801 | 12/1997 | Chien ....................................... 442/364 |

FOREIGN PATENT DOCUMENTS

| | | |
|---|---|---|
| 665315 | 8/1995 | European Pat. Off. . |
| 9425658 | 11/1994 | WIPO . |
| 9613319 | 5/1996 | WIPO . |
| 9702378 | 1/1997 | WIPO . |
| 9724482 | 7/1997 | WIPO . |

*Primary Examiner*—James J. Bell
*Attorney, Agent, or Firm*—Speckman Pauley Petersen & Fejer

[57] ABSTRACT

A 3-dimension thermoformed bicomponent fiber nonwoven material comprising a lofty bicomponent material layer forming a plurality of peaks separated from one another by channels and having a basis weight in the range of about 0.5 to 7.0 ounces per square yard. The bicomponent material layer comprises a structural component and a heat activatable adhesive component suitable for thermoforming. Also disclosed are various configurations of this material suitable for use in absorbent personal care articles such as sanitary napkins, disposable diapers, incontinent-care pads and the like.

40 Claims, 4 Drawing Sheets

ULTRA RESILIENT THREE-DIMENSIONAL NONWOVEN FIBER MATERIAL AND PROCESS FOR PRODUCING THE SAME

BACKGROUND OF THE INVENTION

1. Field of the Invention

This invention relates to a bicomponent fiber nonwoven material which, due to its shape as well as the conditions for its production, exhibits ultra high resiliency. These materials are suitable for use as a body-side liner material for personal care absorbent articles including diapers, feminine pads, incontinence garments, and training pants, as inserts for personal care absorbent products, and as a shell for an absorbent core of such articles. These materials provide for feces separation and containment, air circulation, menses management and containment, and fluid distribution and containment.

2. Description of Prior Art

Absorbent personal care articles such as sanitary napkins, disposable diapers, incontinent-care pads and the like are widely used, and much effort has been made to improve the effectiveness and functionalities of these articles. Thick, flat personal care articles of the past that do not fit the shape of the human body and do not conform to the movements of the user have been largely replaced by resiliently conforming 3-dimensional, body-shaped articles.

Diaper dermatitis is a skin condition resulting from the prolonged contact of wet occlusive diapers with the skin of the wearer. This prolonged contact can lead to excessive hydration of the outermost skin layer, thereby reducing the skin's ability to function as a barrier. As a result, there is an increase in the permeation of irritants, susceptibility of the skin to physical damage, and invasion of the skin by microorganisms. Maintaining a normal skin hydration level helps the skin maintain its optimum barrier properties. Thus, it is important that personal care absorbent articles, to the extent possible, prevent excessive skin hydration while containing body exudates and providing a soft, dry and comfortable feel to the wearer.

Current occlusive absorbent garments with flat liners hold body exudates against the skin of the wearer. Heat and moisture are prevented from escaping from the product due to the close fitting nature of the product design to prevent leakage. This problem is most severe in the insult region of personal care absorbent products. The flat liner provides a high contact area with the skin which can act as a pathway to conduct back to the skin free liquid that is not locked up by the absorbent core, especially when the product is under pressure at the insult point, because the flat liner cannot provide a sufficient degree of separation of the wearer from the free liquid. In addition, flat liners do not allow the insult region of the personal care absorbent product to communicate with the ambient air to allow humidity to be reduced in the insult region as well as away from the insult region.

Numerous means for achieving communication of the interior region of a personal care absorbent product with the ambient air, including breathable backsheets, waste vents, and leg vents, are known. However, these methods suffer from a variety of difficiencies, rendering them less effective than desired to achieve normal, unoccluded skin hydration levels. For example, breathable backsheets provide a pathway for drying through the backsheet to the interior of the absorbent product. However, the wet absorbent can hinder true communication between the skin and the ambient air. In addition, waist and leg vents through the backsheet tend to either be occluded against the skin or provide leakage pathways.

Other known methods include the use of folded absorbent cores or layers under the liner to dry the liner, that is the skin contact layer. However, these methods require undesireable process options and economics and do not truly allow the ambient air to dry the skin of the wearer; rather, they merely dry the skin contact layer. As a result, there is a need for a material that can be used for, among other things, a liner material for personal care absorbent products such as diapers, training pants, incontinence garments, sanitary napkins, bandages and the like, which is capable of reducing the humidity in the insult region of the product and the skin hydration level of the wearer.

SUMMARY OF THE INVENTION

Accordingly, it is an object of this invention to provide a nonwoven material having resiliency, strength, and cloth-like properties.

It is yet another object of this invention to provide a process for producing a nonwoven material having resiliency, strength, and cloth-like properties.

It is an object of this invention to provide a nonwoven material suitable for use in a personal care absorbent product which allows the insult region to communicate through air passageways or channels with ambient air to provide reduced humidity in all regions in the personal care absorbent product.

These and other objects are achieved by a 3-dimensional thermoformed bicomponent fiber nonwoven material comprising a lofty bicomponent material layer which forms a plurality of peaks. The peaks are separated from one another by channels. The basis weight of the nonwoven material in accordance with this invention is in the range of about 0.5 to 7.0 ounces per square yard (about 17 to about 240 grams per square meter). The bicomponent layer of this material comprises a structural component and a heat-activatable adhesive component suitable for thermo-forming.

The process for producing a 3-dimensional resiliently compressible, bicomponent fiber nonwoven material in accordance with this invention, comprises forming a structural fiber component and a heat-activatable adhesive component into a nonwoven web having a basis weight in a range of about 0.5 to 7.0 ounces per square yard. The nonwoven web is heated to a temperature sufficient to melt the heat-activatable adhesive component, which temperature is below the melting temperature of the structural fiber component, resulting in formation of a pliable nonwoven web. The pliable nonwoven web is then shaped to form a shaped web having a plurality of peaks separated from one another by channels. The resulting shaped web is then cooled to solidify the melted heat-activatable adhesive component, resulting in formation of the desired end product.

The foregoing and other features and advantages of this invention will become further apparent from the following detailed description of the presently preferred embodiments, read in conjunction with the examples and drawings. The detailed description, examples and drawings are merely illustrative rather than limiting the scope of the invention being defined by the appended claims and equivalents thereof.

DETAILED DESCRIPTION OF THE PRESENTLY PREFERRED EMBODIMENTS

Figure 1A:
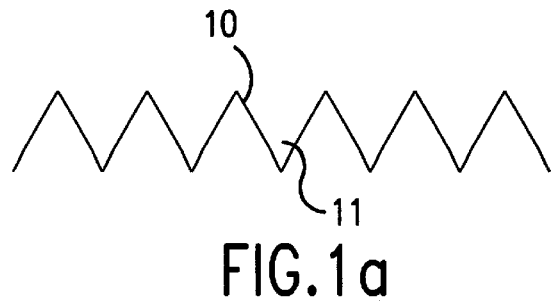
FIGS. 1a–1e are schematic cross-sectional views of a corrugated 3-dimensional thermoformed bicomponent fiber nonwoven materials in accordance with this invention.

The lofty bicomponent material layer of the nonwoven material of this invention has substantially uniformly distributed interfiber bonds and comprises a structural fiber component and a heat-activatable adhesive component. The adhesive component may be added as an external adhesive or may form a portion of the fibers of the nonwoven web as discussed hereinbelow. Suitable fibers for use in this invention are crimped fibers including crimped monocomponent fibers, that is the fibers are fabricated from homogeneous polymer composition, and crimped multi-component conjugate fibers, that is fibers containing at least two component polymer compositions which occupy distinct cross sections along substantially the entire length of the the fibers. Particularly suitable for use in this invention are crimped conjugate spunbond or staple fibers, and most suitable in accordance with another embodiment of this invention are bicomponent conjugate fibers. Of these fibers, multi-component conjugate fibers having component polymers that have different melting points are particularly desirable for the present invention because no additional and extraneous adhesive component is required to bond the nonwoven web, thereby simplifying the nonwoven web manufacturing process.

The crimp level of the fibers may be changed to provide different properties to the web, including different density, strength, softness and texture. In general, highly crimped fibers bonded in accordance with the present invention provide a lofty, soft web. Suitable fibers for the nonwoven material of this invention have at least two crimps per extended inch, preferably between about 2 and about 50 crimps per extended inch, and most preferably between about 3 and about 30 crimps per extended inch, as measured in accordance with ASTM D-3937-82. Suitable spunbond fibers and staple fibers for the present invention have an average diameter from about 5 microns to about 100 microns, preferably from about 10 microns to about 50 microns.

The term "fibers" as used throughout this specification and the claims refers both to staple fibers and to filaments, which are continuous fibers. The term "spunbond fibers" refers to fibers formed by extruding molten thermoplastic polymers as filaments from a plurality of relatively fine, usually circular, capillaries of a spinneret, and then rapidly drawing the extruded filaments by an eductive or other well-known drawing mechanism to impart molecular orientation and physical strength to the filaments. The drawn fibers are deposited onto a collecting surface in a highly random manner to form a nonwoven web having essentially a uniform density. The nonwoven web is then bonded to impart physical integrity and strength. Processes for producing spunbond fibers and webs therefrom are disclosed, for example, in U.S. Pat. No. 4,340,563 and U.S. Pat. No. 3,692,618. The term "staple fibers" refers to noncontinuous fibers. Staple fibers are produced with a conventional fiber spinning process and then cut to a staple length, preferably in the range of about 1 inch to about 8 inches. Such staple fibers are subsequently carded, wet-laid, or air-laid and then thermally bonded to form a nonwoven web.

Suitable nonwoven webs for use in the 3-dimensional bicomponent fiber nonwoven material of this invention can be produced from conjugate fibers containing component polymers having different melting temperatures such that the lower melting temperature polymer, the adhesive component, can be melted and thus rendered adhesive while allowing the higher melting temperature polymer, the structural component, to maintain the physical integrity and structure of the nonwoven web. The melted adhesive component polymer autogenously adheres to adjacent fibers, especially at the cross-over contact points. Consequently, the melting temperature differential between the adhesive component and the structural component is at least about 5° C., preferably at least about 10° C. In accordance with this invention, suitable conjugate fibers should have the adhesive component polymer at least partially exposed to the surface along substantially the entire length of the fibers. In accordance with one preferred embodiment of this invention, the conjugate fibers comprise from about 20% to about 80% by weight of the adhesive polymer. In accordance with a particularly preferred embodiment of this invention, said conjugate fibers comprise in the range of about 40% to about 60% by weight of the adhesive polymer. The crimped fiber nonwoven web of this invention is bonded to have a lofty structure that contains interfiber bonds throughout the web. Bonding processes useful for the present invention should raise the temperature of the deposited nonwoven web to activate its adhesive component without applying significant compacting pressures on the web. The melted or activated adhesive component polymer forms substantially uniform interfiber bonds throughout the web, particularly at the fiber crossover contact points, providing a lofty nonwoven web that is soft but strong and having a high level of resiliency. Illustrative articles that can be produced using the nonwoven material of this invention include personal-care absorbent products and components thereof, such as body-conforming sanitary napkin shells over an absorbent core, shape-retaining diaper components, incontinent care products and the like.

Bonding processes suitable for use in connection with this invention include through-air bonding, hot-oven bonding, and infrared-heater bonding processes. Particularly preferred are through-air bonding processes. The time and temperature of the bonding process can be varied to accommodate the temperature and speed limitations of the selected bonding equipment. It is important, however, that the combination of duration and temperature of the bonding process is sufficiently long and high so as to melt the adhesive component of the web but not sufficiently long and high so as to melt the structural component, thereby preserving the physical and dimensional integrities and preventing shrinkage of the fiber webs. For example, when polypropylene and polyethylene are used as the component polymers for a conjugate-fiber nonwoven web and a through-air bonding process is used, the air flowing through the through-air bonder may have a temperature between about 230° F. and about 280° F. at a velocity from about 100–500 feet per minute, and the dwell time of the web in the bonder is desirably less than about 6 seconds.

Monocomponent suitable for the present invention can be produced from a wide variety of thermoplastic polymers that are known to form fibers.

Similarly, conjugate fibers can be formed within a wide variety of combinations of thermoplastic polymers provided, as indicated above, that the selected polymers have sufficiently different melting points, preferably having a melting point difference of at least about 10° C., and, desirably, having different crystallization, solidification and/or elastic properties. The melting point difference between the selected polymers facilitates the heat activated bonding process, the differences in the crystallization and solidification properties promote fiber crimping, especially crimping through heat activation of latent crimps, and the difference in elastic properties facilitates the mechanical crimp-forming process. Suitable polymers are selected from the group consisting of polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium polyethylene, high density polyethylene and blends thereof; polypropylene; polybutylene and copolymers as well as blends thereof. Additionally, the suitable fiber forming polymers may have thermoplastic elastomers blended therein. Of these suitable polymers, particularly suitable polymers to the structural component of suitable conjugate fibers include polypropylene and copolymers of polypropylene and ethylene, and particularly suitable polymers for the adhesive component of the conjugate fibers include polyethylenes, more particularly linear low density polyethylene, and high density polyethylene. In addition, the adhesive component may contain additives for enhancing the crimpability and/or lowering the bonding temperature of the fibers, and enhancing the abrasion resistance, strength and softness of the resulting webs. For example, the adhesive polymer component may contain about 5 to about 20% by weight of a thermoplastic elastomer such as ABA' block copolymer of styrene, ethylene-butylene and styrene. Such copolymers are commercially available. Another group of suitable additive polymers is ethylene alkyl acrylate copolymers, such as ethylene butyl acrylate, ethylene methyl acrylate and ethylene ethyle acrylate, and the suitable amount to produce the desired properties is from about 2 weight percent to about 50 weight percent based on the total weight of the adhesive polymer component. Still other suitable additive polymers include polybutylene copolymers and ethylene-propylene copolymers.

Nonwoven materials suitable for use in the present invention have a basis weight preferably in the range of about 0.5 to about 7.0 ounces per square yard (osy), that is about 15 to 240 grams per square meter.

The heat-activatable adhesive component of the nonwoven material of this invention may be an external hot-melt adhesive in the form of a powder or a liquid which is applied or sprayed so as to be distributed throughout the web. Adhesives particularly suitable for the present invention are conventional, thermoplastic hot-melt adhesives, such as polyethylene-, polyamide-, polyester- and ethylene-vinyl acetate copolymer-based hot-melt adhesives, which adhesives as previously stated are selected to have a melting temperature below the melting temperature of the structural component of the material.

In order to overcome the disadvantages of current disposable absorbent garments, it is desired to provide a material suitable for use as a liner in such garments that will allow the insult region and areas away from the insult region to communicate through air passageways or channels with ambient air to provide reduced humidity in all regions in the personal care absorbent product and, at the same time, provide suitable absorbent properties to provide low leakage in a personal care absorbent product even when subjected to the pressure of the wearer. In addition, the liner material should have a soft, dry feel and contain minimal free liquid at the skin contact regions after insult to reduce wearer discomfort and skin hydration. In accordance with one embodiment, the nonwoven material of this invention is imparted with wettability by addition of a surfactant.

To allow ambient air to reach the skin of the wearer, the nonwoven material of this invention is provided with resilient, crush-resistant raised skin contact areas or peaks and air passageways or channels formed between the raised skin contact areas to provide desired functional characteristics, including humidity reduction, thereby promoting the desired maintenance of normal skin hydration along with the desired absorbency and comfort properties. The structure, geometry and the selection of the construction materials that form the overall material are important aspects of this invention.

It is another object of this invention to provide a means for separating feces from the skin of the wearer to reduce irritation of the skin. Separation of the feces from the skin of the wearer is possible in accordance with this invention due to the ability of the nonwoven material to store the feces in the areas between the raised peaks of the material.

The nonwoven material of this invention may be designed to perform a variety of fluid handling functions. FIGS. 1a–1e show a variety of configurations of nonwoven material in accordance with this invention based upon corrugation of the nonwoven material. The material of the corrugated embodiments shown in FIGS. 1a–1e are a corrugated lofty bicomponent structure having a basis weight of about 0.5 to 7 osy. The material is rendered ultra resilient by the thermoforming process discussed hereinbelow. The preferred number of corrugations in accordance with the embodiments shown in FIGS. 1a–1e is in the range of ½ corrugation per inch to 4 corrugations per inch.

Disposed within peaks 10 of the corrugated nonwoven material in accordance with one preferred embodiment of this invention is an alternate component 12 which is dependent upon the particular application for the nonwoven material. The purpose of these alternate components is typically to absorb liquids entering through the top face of the corrugated layer. Depending on the nature of the alternate component which may include fluff, SAP, fibrous SAP, odor control devices, distribution material and surge material, the material can be designed to hold a liquid passing through the top face of the corrugated nonwoven material and/or transfer all or a portion of it to yet another layer (not shown). Suitable materials for this alternate component include, but are not limited to, cotton fluff, tissue, woven materials, tow, and especially nonwoven materials, as well as combinations thereof. Blends of both natural and synthetic fibers also work well. In accordance with one preferred embodiment of this invention, as shown in FIG. 1c, the corrugated nonwoven material is filled with its own construction material.

Figure 1B:
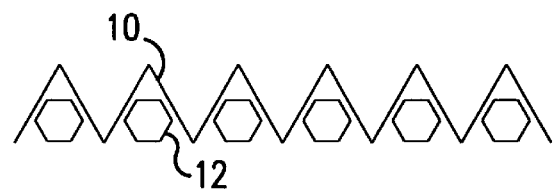
Figure 1C:
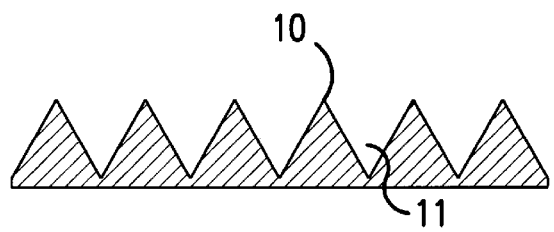

FIG. 1b shows another variation of the corrugated nonwoven material in accordance with one embodiment of this invention wherein the spacing between corrugations is such as to provide a land area 13 at the base of channels 11. In accordance with one preferred embodiment of this invention, the spaces between peaks 10 of the corrugated nonwoven material are at least about 1/16 inch.

Figure 1D:
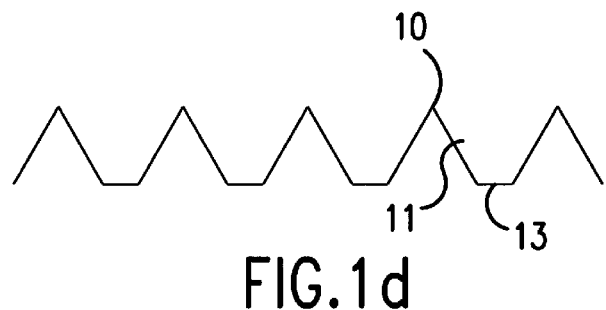
Figure 1E:
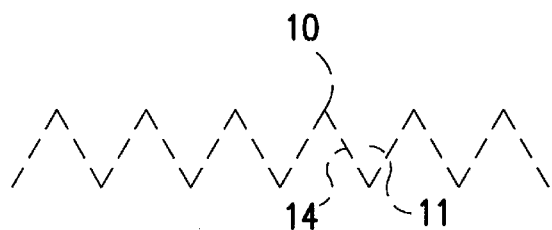

In accordance with a particularly preferred embodiment of this invention particularly suitable for feces separations/ containment and menses management/containment, the nonwoven material forms a plurality of slits or apertures 14 as shown in FIG. 1e which improve the ability of the material to pass the body exudates through the nonwoven material layer to a distribution or surge material disposed below the nonwoven material layer in a personal care absorbent product. It will be apparent to those skilled in the art that any and all of the features of the corrugated nonwoven material shown in FIGS. 1a–1d including the addition of alternate components 12 such as fluff, SAP, fibrous SAP, odor control devices, distribution material and surge material, as well as the formation of land areas or valleys 13 at the base of channels 11 are equally applicable to this embodiment.

FIGS. 2a–2e show alternative embodiments of the 3-dimensional thermoformed bicomponent fiber nonwoven material of this invention. In accordance with this embodiment, peaks 10 are in the form of pleats formed by creating a plurality of pairs of inwardly facing first and second folds 15, 16 from a single layer material that is continuous in the cross direction. The nonwoven material of this embodiment is in the same basis weight range as the corrugated nonwoven materials shown in FIGS. 1a–1e, namely in the range of about 0.5 to 7 osy. In addition, the pleating density is in the same range as the corrugation density of the corrugated nonwoven material, containing ½ pleat per inch to 4 pleats per inch. As in the case of the corrugated nonwoven material, the structure of this embodiment is also ultra resilient as a result of refusing of the fibers comprising the nonwoven material during thermoforming.

Figure 2A:
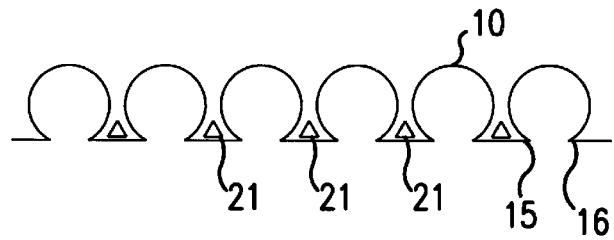
FIGS. 2a–2e are schematic diagrams showing a cross-sectional view of a 3-dimensional thermoformed bicomponent fiber nonwoven material in accordance with other embodiments of this invention.
Figure 2B:
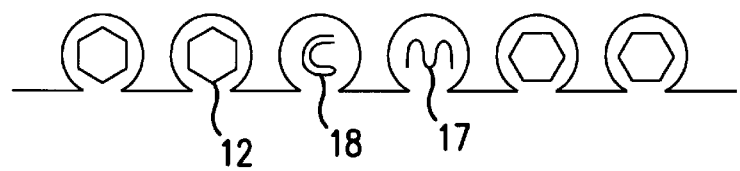

A variation of the pleated nonwoven material in accordance with this invention is shown in FIG. 2b in which alternate components 12 are disposed within the pleats. Suitable alternate components 12 include, but are not limited to, surge, distribution, SAP, fluff, fibrous SAP, odor control devices, desiccants, or other thermoformed structures. In the center pleats, an already thermoformed double "C" fold 18 or "M" folded material 17 can be added to further increase the resiliency of the fabric. It is within the scope of this invention that only a portion of the nonwoven material of this invention be thermoformed. For example, the pleats forming peak 10 need not be thermoformed where the filler material 12 is, in fact, thermoformed. Alternatively, the pleats may be thermoformed and the filler material not thermoformed.

Figure 2C:
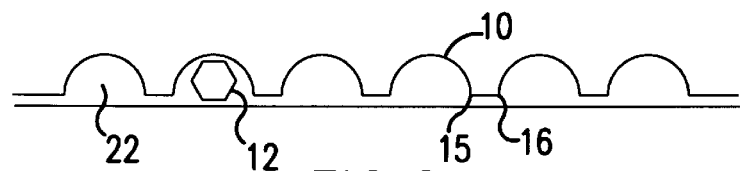
Figure 2D:
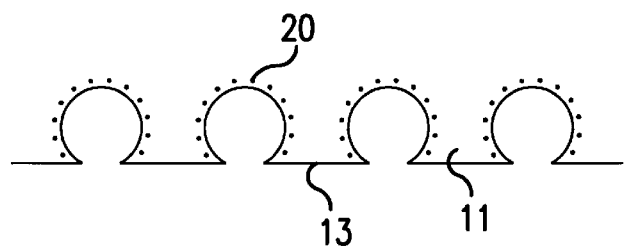

In addition to alternate components disposed within the pleats, active particles 20 as shown in FIG. 2d, such as fluff, SAM distribution material, and any other component that provides utility to the thermoformed nonwoven material can be thermoformed to the surface of peaks 10. Such components 21 as shown in FIG. 2a may also be disposed between peaks 10. These systems provide substantially faster intake rates, lead to reduced leakage, and provide better fit and comfort in use. These systems are also suitable for feces containment.

FIG. 2c shows yet another embodiment of the thermoformed nonwoven material of this invention in which the folds 15, 16 are made in a manner which results in the formation of essentially semicircular peaks. The semicircular peaks 10 of this embodiment are suitable for holding filler material 12 and can be closed on the bottom 22 either by material of the same type as the nonwoven material used in formation of the semicircular peaks 10 or with a meltblown or meltsprayed material sprayed on the bottom surface in a continuous process.

Figure 2E:
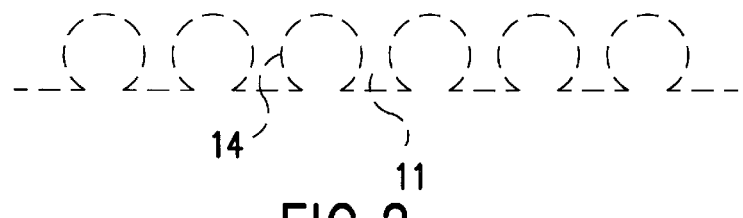

FIG. 2d shows an embodiment of the pleated nonwoven material which corresponds to the corrugated embodiment shown in FIG. 1d in which landing areas or valleys 13 are disposed between adjacent peaks 10. Similarly, FIG. 2e shows an apertured embodiment of the pleated thermoformed nonwoven material of this invention corresponding to the apertured version of the corrugated nonwoven material shown in FIG. 1e.

All of the structures of the thermoformed nonwoven material shown in FIGS. 1a–1e and 2a–2e lend themselves to feces containment between the peaks, that is, containing the feces in the land areas 13. If the peaks 10 are sufficiently close, as in the embodiment shown in FIG. 2a, for example, the feces can be hidden or masked from view and contained for ease of cleanup and diaper removal. In addition, use of the apertured embodiment shown in FIG. 2e permits dewatering of the feces, thereby aiding in separation. The thermoformed nonwoven materials of this invention can function as an inert or as a full length liner.

Due to the increased surface area of a liner material employing the thermoformed nonwoven material structures of this invention, there is a significant reduction in side leakage. The fluid flows into spaces in between the peaks, thereby reducing or eliminating the tendency for fluid to run off the liner.

Figure 3A:
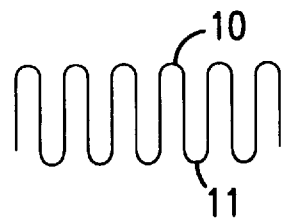
FIGS. 3a–3i are cross-sectional views of alternate embodiments of the 3-dimensional thermoformed bicomponent fiber nonwoven material in accordance with this invention.
Figure 3B:
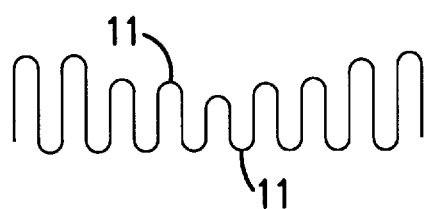

Additional 3-dimensional shapes for use in connection with the ultra resilient, thermoformed nonwoven materials of this invention are shown in FIGS. 3a–3i. These shapes are all capable of at least two of the following functions: leakage reduction, feces leakage reduction, feces separation, feces containment, surge functionality, and potentially, skin wellness. FIGS. 3a–3b show one configuration of corrugated nonwoven material in which the corrugation is a wave defined by peaks 10 and channels 11. If this structure is utilized as a liner material, it can provide side leakage protection by channeling fluid through channels 11. The structures provide faster intake rates due to the increased surface area of the fabric against the body.

Figure 3C:
Figure 3D:
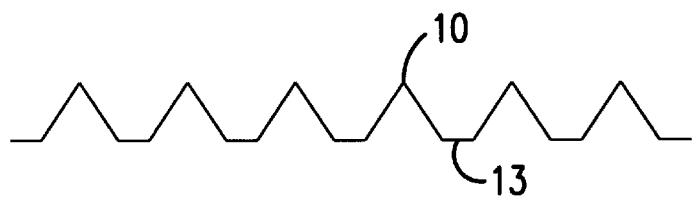
Figure 3E:
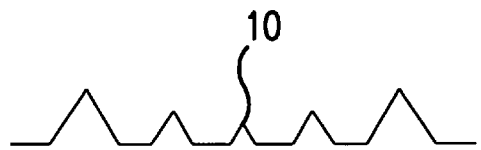

FIG. 3b shows a corrugated wave structure in which the corrugations are concave. The larger corrugation/waves on the outside edges of the material act as barriers to the flow of fluid and thus aid in the prevention of side leakage. In addition, this structure can also channel feces through the channels 11. Thus, multiple functionalities are provided by this embodiment. FIG. 3c shows a similar concave structure for a more conventional corrugated material. FIGS. 3d–3e show structures corresponding to the structure shown in FIG. 1d in which land areas 13 are disposed between the peaks 10. The embodiment shown in FIG. 3 is merely a concave version of the embodiment shown in FIG. 3d in which the height of peaks 10 is lower toward the center of the structure compared to the outer edges of the structure.

Figure 3F:
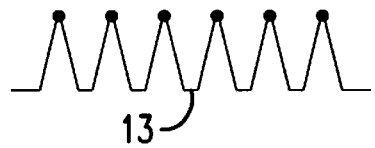
Figure 3G:
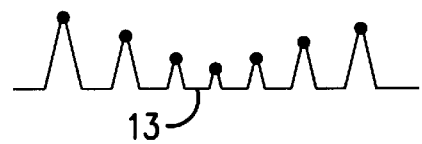

A tree structure in which feces can be enclosed within the land areas or ridges 13 are shown in FIGS. 3f and 3g. Side leakage for urine and feces is reduced, particularly where the "trees" along the outer edges of the material are higher than towards the center of the material.

Figure 3H:
Figure 3I:

Finally, FIGS. 3h–3i show a loop structure which, depending on the stiffness, can be used to contain feces in the deep canals within the structure as well as providing separation from the skin. Additional functional materials including fluff and SAP, distribution material, odor control devices, etc. can be placed within the loop-like channels and sealed to provide a total absorbent system with feces control and urine leakage control.

Figure 4:
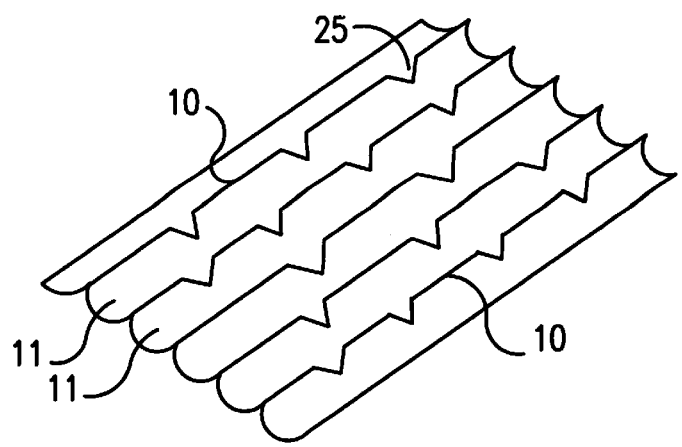
FIG. 4 is a schematic diagram showing a thermoformed nonwoven material having peaks and channels, where the peaks are notched to provide better handling of viscous fluids in accordance with one embodiment of this invention.

In accordance with yet another embodiment of this invention as shown in FIG. 4, the thermoformed nonwoven material comprises a plurality of peaks 10 with channels 11 disposed therebetween. The peaks 10 form a plurality of notches 25 thereby providing better handling of viscous fluids, for example runny feces. The notches 25 sufficiently allow runny feces to flow into all the channels 11.

The process for producing the 3-dimensional thermoformed bicomponent fiber nonwoven material in accordance with this invention comprises forming a structural fiber component and a heat-activatable adhesive component into a nonwoven web having a basis weight in a range of about 0.5 to 7.0 osy. The nonwoven web is then heated to a temperature sufficient to melt the heat-activatable adhesive component without melting the structural fiber component, thereby rendering the nonwoven web pliable. The pliable nonwoven web is then shaped to form a shaped web having a plurality of peaks separated from one another by channels. The shaped web is then cooled to solidify the melted heat-activatable adhesive component.

While the embodiments disclosed herein are presently considered to be preferred, various modifications and improvements can be made without departing from the spirit and scope of the invention. The scope of the invention is indicated by the appended claims, and all changes that fall within the meaning and range of equivalents are intended to be embraced therein.

We claim:

1. A 3-dimensional thermoformed bicomponent fiber nonwoven material comprising:
a lofty bicomponent material layer forming a plurality of peaks, said peaks separated from one another by channels, and having a basis weight in a range of about 0.5 to 7.0 osy, and said bicomponent layer comprising a structural component and a heat-activatable adhesive component suitable for thermoforming.

2. A nonwoven material in accordance with claim 1, wherein said structural component comprises a fiber-forming thermoplastic polymer.

3. A nonwoven material in accordance with claim 2, wherein said thermoplastic polymer is selected from the group consisting of polyolefins, polyamides, polyesters, polycarbonates, polystyrenes, thermoplastic elastomers, fluoropolymers, vinyl polymers, and blends and copolymers thereof.

4. A nonwoven material in accordance with claim 1, wherein said structural fiber component is spunbond fibers.

5. A nonwoven material in accordance with claim 1, wherein said structural fiber component is staple fibers.

6. A nonwoven material in accordance with claim 1, wherein said adhesive component is a hot-melt adhesive having a melting temperature lower than a structural component melting temperature.

7. A nonwoven material in accordance with claim 1, wherein said structural component and said heat-activatable adhesive component are conjugate fibers.

8. A nonwoven material in accordance with claim 1, wherein said lofty bicomponent material is corrugated.

9. A nonwoven material in accordance with claim 6, wherein a corrugation pattern of said lofty bicomponent is selected from the group consisting of uniform sawtooth, concave sawtooth, uniform wave, concave wave, uniform ridge, concave ridge, uniform tree, concave tree, uniform loop, and concave loop.

10. A nonwoven material in accordance with claim 9, further comprising at least one additional component selected from the group consisting of fluff, SAP, fibrous SAP, odor control ingredients, distribution material and surge material.

11. A nonwoven material in accordance with claim 10, wherein said at least one additional component is disposed within the peaks of said corrugated lofty bicomponent material layer.

12. A nonwoven material in accordance with claim 10, wherein said at least one additional component comprises a material suitable for thermoforming.

13. A nonwoven material in accordance with claim 9, wherein a height of said peaks is variable in a range of about ½ inch to 2 inches.

14. A nonwoven material in accordance with claim 9, wherein a distance between said peaks is at least about 1/16 inches.

15. A nonwoven material in accordance with claim 1, wherein said peaks are formed by pleating of said lofty bicomponent material layer.

16. A nonwoven material in accordance with claim 14 further comprising at least one additional component selected from the group consisting of fluff, SAP, fibrous SAP, odor control means, distribution material and surge material.

17. A nonwoven material in accordance with claim 16, wherein said at least one additional component is disposed within said peaks.

18. A nonwoven material in accordance with claim 17, wherein said at least one additional component comprises a material suitable for thermoforming.

19. A nonwoven material in accordance with claim 15, wherein a pleating density of said pleats is in a range of about ½ pleat to 4 pleats per inch.

20. A nonwoven material in accordance with claim 1, wherein said peaks form a plurality of slit-like apertures.

21. A nonwoven material in accordance with claim 1 further comprising a surfactant, said surfactant imparting wettability to said material.

22. A liquid absorbing liner material comprising:
a lofty bicomponent material layer forming a plurality of peaks, said peaks separated from one another by channels, and having a basis weight in a range of about 0.5 to 7.0 osy, and said bicomponent layer comprising a structural fiber component and a heat-activatable adhesive component suitable for thermoforming.

23. A liquid absorbing liner material in accordance with claim 22, wherein said structural fiber component is spunbond fibers.

24. A liquid absorbing liner material in accordance with claim 22, wherein said structural fiber component is staple fibers.

25. A liquid absorbing liner material in accordance with claim 22, wherein said adhesive component is a hot-melt adhesive.

26. A liquid absorbing liner material in accordance with claim 22, wherein said structural fiber component and said heat-activatable adhesive component are conjugate fibers.

27. A liquid absorbing liner material in accordance with claim 22, wherein said lofty bicomponent material is corrugated.

28. A liquid absorbing liner material in accordance with claim 27, further comprising at least one additional component selected from the group consisting of fluff, SAP, fibrous SAP, odor control means, distribution material and surge material.

29. A liquid absorbing liner material in accordance with claim 28, wherein said at least one additional component is disposed within the peaks of said corrugated lofty bicomponent material layer.

30. A liquid absorbing liner material in accordance with claim 28, wherein said at least one additional component comprises a material suitable for thermoforming.

31. A liquid absorbing liner material in accordance with claim 27, wherein a height of said peaks is variable in a range of about ½ inch to 2 inches.

32. A liquid absorbing liner material in accordance with claim 27, wherein a distance between said peaks is at least about 1/16 inches.

33. A liquid absorbing liner material in accordance with claim 22, wherein said peaks are formed by pleating of said lofty bicomponent material layer.

34. A liquid absorbing liner material in accordance with claim 33 further comprising at least one additional component selected from the group consisting of fluff, SAP, fibrous SAP, odor control means, distribution material and surge material.

35. A liquid absorbing liner material in accordance with claim 34, wherein said at least one additional component is disposed within said peaks.

36. A liquid absorbing liner material in accordance with claim 34, wherein said at least one additional component comprises a material suitable for thermoforming.

37. A liquid absorbing liner material in accordance with claim 33, wherein a pleating density of said pleats is in a range of about ½ pleat to 4 pleats per inch.

38. A liquid absorbing liner material in accordance with claim 22, herein said peaks form a plurality of slit-like apertures.

39. A liquid absorbing liner material in accordance with claim 22 further comprising a surfactant, said surfactant imparting wettability to said material.

40. A process for producing a 3-dimensional resiliently compressible, bicomponent fiber nonwoven material from a structural fiber component and a heat-activatable adhesive component comprising:

forming said structural fiber component and said heat-activatable adhesive component into a nonwoven web having a basis weight in a range of about 0.5 to 7.0 osy;

heating said nonwoven web to melt said heat-activatable adhesive component without melting said structural fiber component, rendering said nonwoven web pliable;

shaping said pliable nonwoven web to form a shaped web having a plurality of peaks separated from one another by channels; and cooling said shaped web to solidify said melted heat-activatable adhesive component.

* * * * *